United States Patent
Kumakhov

(10) Patent No.: US 6,678,352 B1
(45) Date of Patent: Jan. 13, 2004

(54) ANTI-SCATTERING X-RAY RASTER

(76) Inventor: Muradin Abubekirovich Kumakhov, UL. Narodnogo Opolcheniya, D. 35, KV. 55 Moscow, 123298 (RU)

( * ) Notice: Subject to any disclaimer, the term of this patent is extended or adjusted under 35 U.S.C. 154(b) by 0 days.

(21) Appl. No.: 09/744,467
(22) PCT Filed: May 19, 2000
(86) PCT No.: PCT/RU00/00184
§ 371 (c)(1), (2), (4) Date: Apr. 5, 2001
(87) PCT Pub. No.: WO00/73772
PCT Pub. Date: Dec. 7, 2000

(30) Foreign Application Priority Data

May 28, 1999 (RU) ............................. 99111272

(51) Int. Cl.$^7$ ................................. G21K 1/00
(52) U.S. Cl. ...................... 378/154; 378/155
(58) Field of Search ................. 378/154, 145, 378/147

(56) References Cited

U.S. PATENT DOCUMENTS

| | | |
|---|---|---|
| 4,866,744 A | 9/1989 | Yoshida |
| 4,969,176 A | 11/1990 | Marinus |
| 5,303,282 A | 4/1994 | Kwasnick et al. |
| 5,418,833 A * | 5/1995 | Logan .................. 378/154 |
| 5,557,650 A * | 9/1996 | Guida et al. ........... 378/154 |
| 5,570,408 A | 10/1996 | Gibson |
| 5,712,483 A | 1/1998 | Boone et al. |
| 6,252,938 B1 * | 6/2001 | Tang .................... 378/154 |

FOREIGN PATENT DOCUMENTS

| | | |
|---|---|---|
| EP | 0 087 844 A2 | 2/1983 |
| EP | 0 087 844 B1 | 11/1987 |
| RU | 2098798 | 8/1996 |

* cited by examiner

*Primary Examiner*—Louis Arana
(74) *Attorney, Agent, or Firm*—McGuireWoods LLP

(57) ABSTRACT

An anti-scatter X-ray raster provides suppression of secondary scattered Compton radiation thus improving image contrast. The anti-scatter X-ray raster comprises a plurality of tubular channels made of an X-ray absorbing material. The tubular channels are spliced together to form a cellular structure. The largest cross size (d) of a singe channel its length (H) meet a relationship $2d/H > \theta_c$, where $\theta_c$ is a critical angle of total external reflection of X-rays from the material forming the walls of the tubular channels. The cross-section of the tubular channels need not be circular but may be, for example triangular or hexagonal. In a non-focused raster embodiment all of the longitudinal axis of the channels are parallel. In focused embodiments, the longitudinal axis of the channels are radially angled such that if extended they would meet at the X-ray source point.

33 Claims, 3 Drawing Sheets

US 6,678,352 B1

ANTI-SCATTERING X-RAY RASTER

BACKGROUND OF THE INVENTION

1. Field of the Invention

The present invention relates to roentgenoscopy and, more particularly, to medical X-ray diagnostic and so called X-ray flaw detection or anti-scatter X-ray rasters (grids), which filter a radiation, transmitted through an object toward a detecting device, and absorb a Compton secondary radiation.

2. Description of the Prior Art

X-rays experience an increase in wavelength due to a reduction in energy after being scattered through an angle. This phenomena is referred to a the Compton scattering or Compton secondary radiation. This Compton secondary radiation occurs when X-raying the internal structure of objects in medicine and industry and is the main factor which decreases contrast and degrades the quality of X-ray images.

A high probability of forming quanta of a secondary radiation is characteristic of the Compton effect. That is, there can be several photons of a secondary scattered radiation for every photon of a radiation falling on the object under study which is formed by a primary X-ray source. This significantly reduces quality of the resultant image because of the diffuse nature of the secondary radiation. A purpose of the present invention is to eliminate photons of the secondary Compton radiation, which are moving in a different direction as photons of the primary radiation source.

This problem could be solved by using an anti-scatter raster, having the ability to pass through the photons of the primary radiation as well as that photons of a secondary Compton radiation, which are moving is a direction approximately the same as a primary photons.

Prior art anti-scatter rasters comprise a grid, placed between the object under study and the means for detecting. The grid comprises strips made of a material which can absorb the secondary Compton radiation. The length of strips exceed the distance between them by several times. (see, for example, Chan H.-P., Frank P. H., Doi K., Iida N., Higashida Y. Ultra-High-Strip-density Radiographic Grids: A New Anti-scatter Technique for Mammography. "Radiology", volume 154, Number 3, March 1985, pp. 807–815).

The strips of the grid are generally oriented in the direction parallel to the direction of spreading of the primary radiation. It means that this primary radiation easily passes through the grid. In contrast the Compton secondary radiation is absorbed by the grid. Intensity of the primary radiation is slightly reduced because of the limited transparency of the grid due to the thickness of the strips.

A level of suppression of the secondary Compton radiation is defined by the relationship between a size of the strips in the direction of spreading primary radiation to a distance between neighboring strips. This parameter, called the aspect relationship, defines an value of the angle of deviation of photons of secondary radiation from direction of spreading photons of primary radiation. The greater the aspect relationship, the less is the angle, and subsequently the less the amount of photons of the secondary radiation reach a detecting device, which improves the contrastive quality of an image in the center. However, the brightness and contrast of a peripheral or edges of the image are decreased.

To avoid this negative effect, a grid can be made focused, which means the strips are not parallel to each other, but have an increasing radial angle from the center of the grid to the edges of the grid. The strips are placed in such a way that they provide a parallelism of their planes to the direction of photons of passed through the object under study. In a focused grid, the planes of all strips are oriented to point to the source of a primary radiation, which ideally may be represented as a point source. Thus radiation emanating from the point source spreads parallel with the axial direction of the strips. (see for example, Physics of image visualizing in medicine. Ed. by S. Webb. Moscow, "Mir", 1991, volume 1, pp. 131–133).

Despite the fact that the above mentioned texts describe the usage of an anti-scatter grid only for medical purposes, the general concept of eliminating a secondary radiation is applicable as well for any X-ray applications including internal industrial structures or non-biological objects.

Manufacturing of an anti-scatter raster faces the problem of placing thin strips made of absorbing material a small distance from each other with the precision of their plane orientation. Moreover, the strips have a thickness associated with them. Thus the cross-sectional area of the strips due to the strip thickness has the negative effect of also decreasing the transparency of a grid for a primary radiation. This diminishing of transparency could be compensated for by increasing of intensity of a primary radiation or increasing exposure time. However, both of these measures are undesirable because it increases the radiation dose, which is particularly bad if the object under study is a human patient.

Using thinner strips would of course allow more primary radiation to pass. However, using thinner strips in the grid causes trouble since thinner strips are not as structurally robust. Thus, spacers made of an X-ray transparent material should be placed between absorbing strips to provide necessary stiffness and mechanical strength. However, spacers are problematic in the case of a focused grid since the spacers are required to have a varying thickness along a direction of spreading of radiation (i.e. they must be tapered).

The usage of spacers causes additional losses of intensity of a radiation passed to the detecting device. This in turn causes the above said negative impacts, which require increasing the power of a primary radiation or exposure time. This of course increases the irradiation dose to the object under study as well as maintenance personnel. The Bucky factor characterizes this increase, and according the data of a source Chan et al., supra, it is 2 to 8, and in source Webb, supra, the values are in limits of 2 to 4.5.

According to source Chan et al. actual obtainable distance between the strips is on the order of 150 μm, and according to source Webb it is between 67 to 150 μm.

In the prior art, if an anti-scatter raster is made of strips, the channels for transporting the primary X-rays passed through an object are slots. As a result the secondary radiation which is traveling parallel to the walls of slots (i.e. parallel to the strips) or close to them, is not suppressed.

SUMMARY OF THE INVENTION

The present invention overcomes the disadvantages of prior art by increasing the aspect relationship without deteriorating the transparency of an anti-scatter raster for the primary radiation. The invention selects photons of secondary radiation which have an angle exceeding an angle determined by an aspect relationship and deviates from the direction of a primary radiation in any plane. Therefor satisfactory attenuation of intensity of a secondary radiation on the detecting device can obtain even with small aspect relationship. It allows obtaining acceptable results using a non-focused raster, which is easier to produce and does not require placement at a well-defined distance from the source.

The suggested anti-scatter X-ray raster is disclosed in three embodiments, the first one being a focused anti-scatter raster, and the second and third embodiments being of the focused type. A common feature to all three embodiments is a great number of channels for X-rays transporting, and channels of the walls being made of an X-ray absorbing material.

According to the invention, rather than using strips resulting in a slotted structure as in the prior art, the present invention uses a cellular structure realized by using a plurality of tubular channels for X-ray transporting having adjoining walls spliced together. Thus the largest cross size of a single channel (d), and its length (H) satisfies a relationship $2d/H > \theta_c$, where $\theta_c$ is a critical angle of total external reflection of an X-rays from the walls of the channels.

In all three embodiments the walls of tubular channels are made of a material, capable of absorbing X-ray, for instance, of lead glass. They can be made as well of dielectric or metal. Thus the channels can be both hollow and filled with light metal or organic material. The channels can be formed as well by glass mono or polycapillaries.

According to the first embodiment (non-focused raster) the channels have parallel longitudinal axes, and according to the second and third embodiments, (focused raster) the channels have longitudinal axes, which continuations outside a device converge in one point, a focus, where an X-rays source must be when an anti-scatter raster is in usage.

According to the first embodiment the tubular channels for an X-rays transporting can have a form of a cylindrical surface (need not be circular) or a form of a side surface of a prism (need not be regular). The open ends, (i.e., the inputs and outputs of the channels) according to the first embodiment are placed, are parallel planes perpendicular to the longitudinal axes of all channels. The second embodiment differ in that the open ends are placed on different planes having concentrical spheres with a center in a focus (i.e. the center point being the point where continuations of longitudinal axes of the channels would converge).

According to the third embodiment these surfaces (the planes of the inputs and outputs) are planes parallel to each other, being perpendicular to a longitudinal axis of one of the channels, placed in the central zone of an anti-scatter raster.

According to the second as well as to the third embodiment the walls of the channels can be in a form of side surface of a truncated cone or a truncated pyramid, thus the tops of the figures for all channels coincide with a focus. The cones do not need to be circular, and pyramids do not need to be regular.

Besides the above, other specific cases of embodiment of an anti-scatter raster, related to all three variants, are possible.

According to one specific way an anti-scatter raster in cross-section, corresponding to the direction of an longitudinal axis of one of its channels placed in the central zone of a raster (for the raster according to the first embodiment these directions are equal for all channels), has a size, corresponding to the full size of the object under study or to the full size of a part of the object, and in this projection, in particular, it can have a form of rectangle with comparable sizes of its sides.

According to the other specific ways an anti-scatter raster is intended for usage in a scanning system, when a narrow zone of the object under study is irradiated through a slot collimator, being moved with respect to an object, and an anti-scatter raster, placed on the other side of the object under study just opposite a slot of a collimator, moves in synchronism with the slot.

In this case, the anti-scatter raster can be in the form of narrow brick (i.e., box shape) with a great quantity of cells in one direction, and a smaller amount of cells in other direction, being parallel to a slot of a collimator, and in the other direction, being perpendicular to the first direction (i.e. in the direction of moving a slot of a collimator).

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
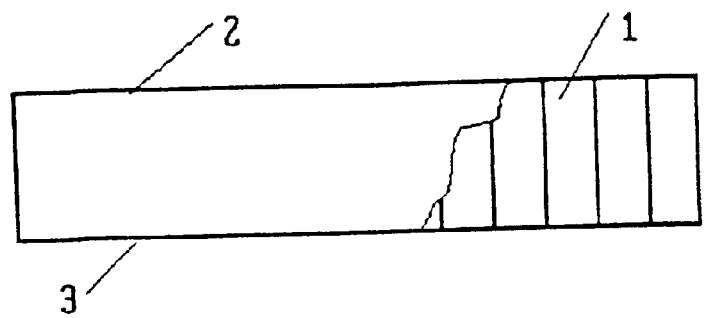
FIG. 1 depicts an anti-scatter raster according to the first embodiment (side view with a longitudinal cross-section of some channels)
Figure 6:
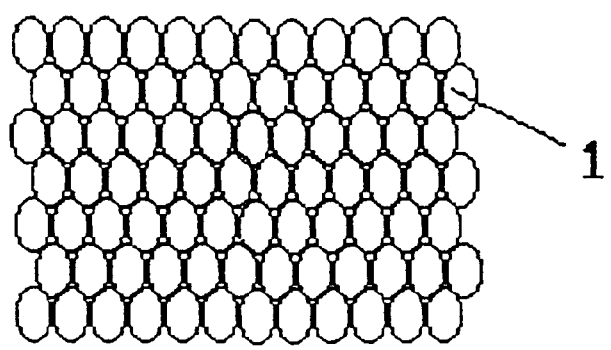
FIG. 6 is shows the cylindrical channels having a round or oval cross-sectional shape.
Figure 7:
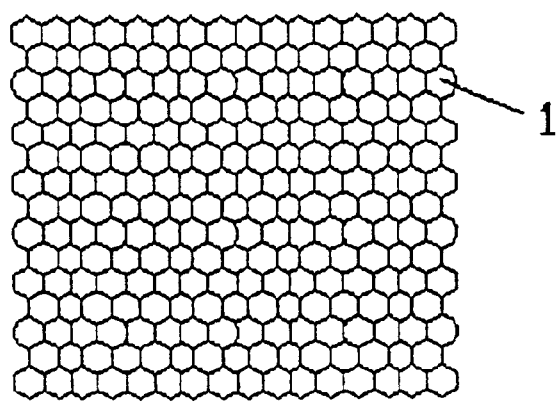
FIG. 7 is a cross-sectional view of the cylindrical channels having a hexagon shape.

Referring now to the drawings, and more particularly to FIG. 1, an anti-scatter X-ray raster according to the first embodiment has a plurality of parallel tubular channels 1 for an X-rays transporting, enclosed by two parallel planes 2, 3, being perpendicular to the longitudinal axes of the channels 1. The channels form a honeycomb structure (hereinafter referred to as a cellular structure). Their walls are in the form of a cylindrical surface or a lateral surface of a prism. FIG. 6 and FIG. 7 depict a form of the said cellular structure as viewed from of inputs or outputs of the channels. FIG. 6 and FIG. 7 illustrate as well embodiments, when the channels in the cross-section are round or oval, or they are in the form of a regular hexagon. In the latter embodiment there are no spaces between sidewalls of the neighboring channels. However the spaces, when they are represented, can operate as channels, and their availability has not an adverse effect on the transparency of a raster.

An anti-scatter raster is produced according to the known technology of producing monolithic X-rays lenses (see, for instance: V. M. Andreevsky, M. V. Gubarev, P. I. Zhidkin, M. A. Kumakhov, A. V. Noshkin, I. Yu. Ponomarev, Kh. Z. Ustok. X-ray waveguide system with a variable cross-section of the sections. The IV-th All Union Conference on Interaction of radiation with Solids (May 15–19, 1990, Elbrus settlement, Kabardino-Balkarian ASSR, USSR). Book of abstracts. Moscow, 1990, pp. 177–178; U.S. Pat.

No. 5,570,408 to Gibson). This technology consists of assembling the tubular stocks of starting diameter, heating up to the temperature of their material softening and drawing with compression in order to obtain a required form of the cross-section of the product. The walls of neighboring channels, which cross size is significantly smaller than a starting cross size of the stocks as a result of stretching and can reach a submicron level, become spliced (i.e., fused).

The mentioned similarity of technologies of producing an anti-scatter raster and a monolithic X-ray lens does not mean that their technical principle is closely related. In an X-ray lens transporting of a radiation is based on the usage of an effect of multiple total external reflection from the interior side of the walls of the channels. Therefore they are designed to provide a capability of such a reflection. In the suggested anti-scatter raster, vice versa, a situation, when an effective component of a radiation passes immediately from the input to the output of a channel and a reflection of this radiation from the walls of the channels has interference affect on the raster coefficients, is ideal. A total absorption of a radiation by the walls of the channels without reflection from them is desirable for a secondary radiation. Following the condition $2d/h > \theta_c$, (at this condition no more than one reflection is possible) provides the lack of multiple reflection of a radiation at its transporting along the channel. In the given inequality a critical angle of total external reflection is the following:

$$\theta_c = h\omega_p/E,$$

where h is a Planck constant, $\omega_p$ is a plasma frequency for the material of the walls of the channels, E is energy of photon of radiation.

Namely, for glass $\theta_c$ [radian]=30/E[eV].

At E=17 keV $\theta_c$ is on the order of $1.8 \times 10^{-3}$ radian.

When an anti-scatter raster is used, it is placed between the object under study and the detecting device. The anti-scatter raster of the first embodiment is not focused and does not provide the identical conditions for passing an effective component of an X-rays for all channels. These conditions are the best for the channels of the central zone of the raster. Photons of a primary radiation, deflected from the direction to the geometrical center of a raster aperture at the angle exceeding the quantity inverse to the aspect relationship, cannot pass through the raster. Therefore the raster should he distanced well away from the source of a primary radiation, where a peripheral zone of the raster is still transparent for a primary radiation, passed through the object under study. Taking into account the above, if an anti-scatter raster is used according to the first embodiment there is no point in obtaining high values of an aspect relationship. Nevertheless if an anti-scatter raster is made as a cellular structure (and not a slot one), it provides good selection of a secondary radiation.

Figure 2:
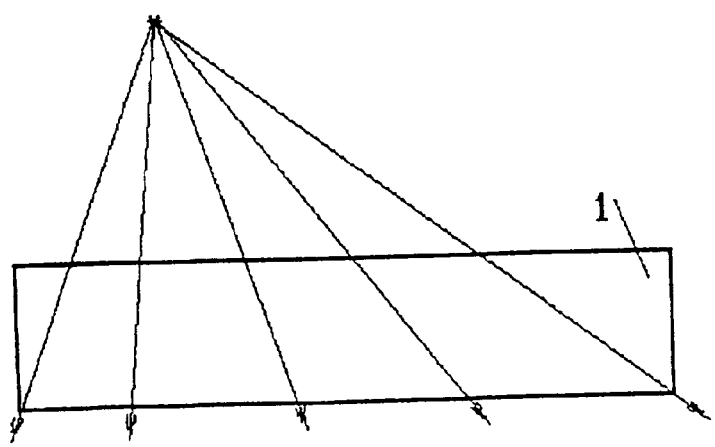
FIGS. 2 and 3 depict a trajectory of photons of a secondary scattered radiation, being capable to reach a detecting device, when a known slot grid and the inventive anti-scatter raster are used, respectively.
Figure 3:
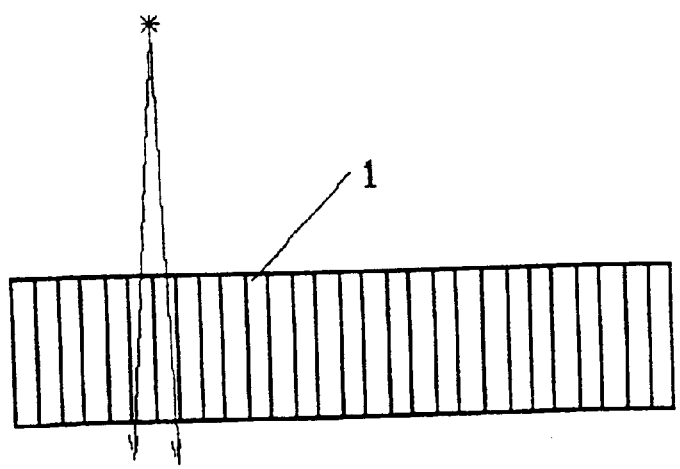

The above is illustrated by FIG. 2 and FIG. 3. FIG. 2 depicts possible trajectories of photons of a secondary scattered radiation from one of the point of the object under study, when they can pass through a slot channel 1 to the detecting device. FIG. 3 depicts a raster, where a slot channel is substituted with channels-cells 1, having the same total size in a FIG. 1. The photons of a secondary radiation, reached a detecting device, have trajectories with smaller angle then shown on the FIG. 2, therefor a possibility of photons reaching the detecting device is reduced.

An amount of suppressing of a secondary radiation has same proportional value to the relation of a length of a slot channel to its width, if the channels have a cross-section size equal to a width of a slot channel.

It is possible to decrease an aspect relationship without the deterioration of a selection of a secondary radiation in comparison with the known slot anti-scatter grids in the limits of value, defined by this achievable gain. Owing to this fact a distance between a raster and a source of primary X-rays can be reduced, and if this distance remains the same a transparency of peripheral channels for a primary radiation in comparison with the known anti-scatter grids of the same sizes can be increased.

Figure 4:
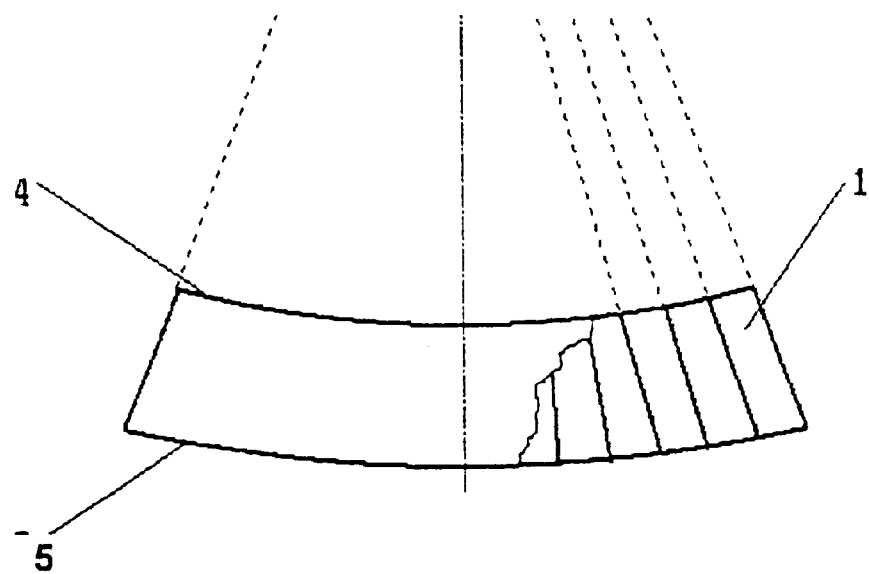
FIG. 4 depicts an anti-scatter raster according to the second embodiment (side view with a longitudinal cross-section of some channels)

The described anti-scatter raster according to the first embodiment is the simplest to produce. Producing a raster according to the second embodiment (FIG. 4) requires additional operations of shaping to make its channels 1 narrow simultaneously with a raster narrowing as from inputs to outputs of the channels. These operations can be carried out by using forming devices with spherical planes, a "plane" raster according to the first variant is fastened between, and the raster is simultaneously heated up to the temperature of the material softening. The input and output planes 4 and 5 are placed on the forming device. The walls of the channels have a form of side surfaces of truncated cones or truncated pyramids with a common top, coinciding with the center of the concentric spherical planes 4 and 5.

A focused anti-scatter raster according to the second embodiment provides good selection of a secondary radiation in combination with a steady transparency along the whole aperture for a primary radiation. Therefore a choice of an aspect relationship in it is not limited by the factors, being taken into account when a raster according to the first embodiment is designed, and it can be realized with full usage of possibilities. Owing to this fact a degree of suppressing a secondary radiation can be very high with corresponding increasing of an image contrast. As the advantages, provided by high aspect relationship, can be realized fully in the raster according to the second embodiment, it is possible to assemble it from polycapillaries, and the sizes of a cross-section of a single channel of a capillary are already very small. In this case before assembling the polycapillaries can be shaped lengthwise to a required narrowing form, thus it is possible to form the raster in pieces rather than as a unit.

Figure 5:
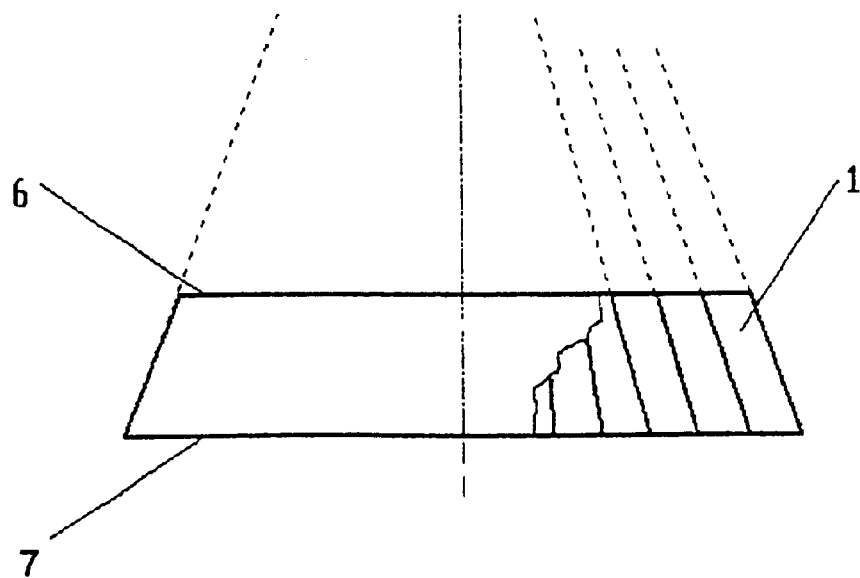
FIG. 5 is a cross-section of the anti-scatter raster according to the third embodiment.

The input and output apertures of an anti-scatter raster according to the second embodiment are non-planar, what makes it inconvenient in use (namely in storing and delivering). This inconvenience is removed in the design of a raster according to the third embodiment (FIG. 5), the channels 1 have the same form as in the raster according to the second variant, but the planes 6 and 7, their inputs and outputs are planar. Such surfaces can be obtained by cutting a raster according to the second variant from two sides (this raster has a "reserve" of a longitudinal size of a channel). Different longitudinal sizes of the channels, increasing to the periphery, are characteristic for the raster according to the third variant. It can cause unequal losses of radiation intensity in the channels, being at different distances from the central zone of the raster, particularly if the channels are not hollow. However the differences at the sizes of the raster and the focal distance (i.e. a distance from the input of the channels of the central zone of the raster to the source of a primary radiation), being characteristic for practical applications, are small.

A form of a cross-section of the channels according to the second and the third embodiments can be the same, as according to the first embodiment (FIG. 6 and FIG. 7). In both embodiments, as well as in the first one, a condition $2d/h > \theta_c$ is followed, and owing to this fact when a radiation is transported along the channels its multiple reflection is lacking.

Figure 8:
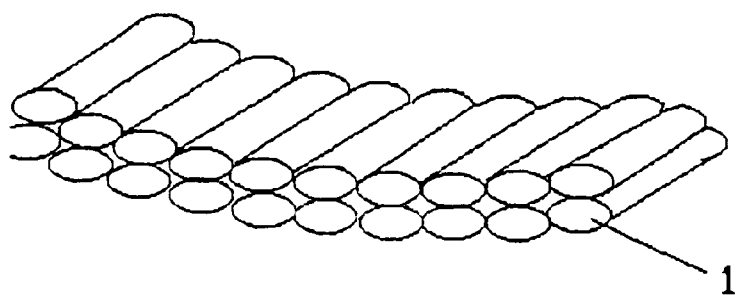
FIG. 8 depicts an anti-scatter raster according to the second embodiment having the cylindrical channels connecting in the form of a brick (i.e., rectangle box shaped).

An anti-scatter raster, intended for the use in a scanning system of X-ray diagnostics or flaw detection, can be made as a narrow brick (parallelepiped shaped) (FIG. 8), and the quantity of channels 1 along its larger side is significantly more than in a perpendicular direction (i.e. in direction of a raster moving when scanning is realized).

Realizing a high aspect relationship may be not to the purpose if an anti-scatter raster is made as a narrow parallelepiped according to the first embodiment, and taking into account a straight path of its moving and the above said reasons. Therefore such a raster can be made with rather large cross size of the channels, placed in one row along the parallelepiped's length.

If an anti-scatter raster is made as a narrow parallelepiped according to the second and third embodiments, i.e. when they are focused, to realize advantages of this method it is reasonable to move the parallelepiped in an arc of a circle with a center in a focus (i.e. in a point where a source of a primary X-rays is placed) in order to keep an orientation of the longitudinal axes of the channels to the source. In this case it is reasonable to realize a high aspect relationship, and a parallelepiped can be made of several rows of channels as cross sizes of the channels are small.

The indexes of a raster in a form of a narrow parallelepiped according to the first embodiment can be improved when a brick of channels is moved in an arc of a circle, as the conditions of a primary radiation passing through a raster will be equal in all points of a trajectory, it is moved along.

The channels for radiation transporting, according to all three embodiments, can be made of glass; lead glass is preferable. It is possible to make the channels of lead or other heavy metals as well. An advantage of these materials is that in this case the walls of the channels can be very thin. For instance, if a raster is used for mammography, when an X-ray tube with molybdenum anode is used as a source (quanta photon energy is E=1.74 keV), the walls may be as thick as 10–20 μm. It increases the transparency of a raster and makes possible to keep a raster immovable as a survey is realized, as the shadows of such thin walls are not practically visible on the film.

Sometimes, in dependence of the energies to be used, it can be reasonable to make the walls of the channels of light metals (for instance aluminum) or dielectrics. It can be realized when a radiation fall on the wall made of heavy metal causes hard secondary radiation, which can reaches an X-ray film or a detector. When light metals and dielectrics are used an emerging secondary radiation is soft and it is absorbed in a air layer of some centimeters thickness.

It is desirable to make the channels hollow in most cases, for instance a raster can be made of glass mono or polycapillaries. In this case a transparency of a raster (a relationship of an open area of the cross-section of a raster to a total area) can reach 80%. Such a high transparency makes possible to decrease an irradiation dose of a patient. A technology of such raster producing is complicated. Therefore sometimes in order to simplify producing it is possible to make a raster with the channels filled with an organic material (for instance, polyvinyl chloride) or light metal, which slightly absorbs a primary radiation, carrying the information about the object under study. The filled channels are less affected by uncontrollable deformations during forming of a raster.

Experimental researches of a raster, produced according to the suggested inventions, show that it is real to produce a device with cross sizes of 20×20 cm² and more. When the raster is made of lead glass, attained transmission factor for an effective component of a radiation is on the order of 0.85. If an aspect relationship H/d is on the order of 60 to 100, attenuation of a scattered radiation on the output of a raster reaches 100 to 1000 times. An image contrast increasing in 4 to 7 times (for instance, in mammographic researches) corresponds to such indexes. Thus the usage of a raster makes possible to decrease an irradiation dose in 3 to 5 times.

While the invention has been described in terms of a single preferred embodiment, those skilled in the art will recognize that the invention can be practiced with modification within the spirit and scope of the appended claims.

I claim:

1. An anti-scatter X-ray raster, for placing between a radiation detector and an object under study, said anti-scatter X-ray raster comprising:

a plurality of channels for X-ray transporting connected together to form a cellular structure, walls of the said channels comprising a material capable of absorbing X-rays, wherein said channels are tubular with the orientation of the walls of all said channels being in a same in a longitudinal direction and the walls are in a form of cylindrical surface or a lateral surface of a prism and form a honeycomb structure and the walls of the neighboring channels are fused with each other; and an input end of said channels and an output end of said channels, wherein the input end and output end of the said channels are placed in two parallel planes, being perpendicular to the longitudinal direction of the said channels, wherein the largest cross size d of a single channel and its length H meet a relationship $2d/H > \theta_c$ where $\theta_c = \hbar \omega_p / E$ is the critical angle of total external reflection of X-rays from the walls of the channels transporting X-rays, for the material of the walls, $\hbar$ is the Planck constant, $\omega_p$ is the plasma frequency of the material of the channels' walls, E is energy of radiation quanta.

2. A raster according to claim 1, wherein the walls of the channels for X-ray transporting comprise lead glass.

3. A raster according to claim 1, wherein the walls of the channels for X-ray transporting comprise metal.

4. A raster according to claim 1, wherein the walls of the channels for X-ray transporting comprise heavy metal.

5. A raster according to claim 1, wherein the walls of the channels for X-ray transporting comprise a dielectric.

6. A raster according to claim 1, wherein the channels for X-ray transporting are hollow.

7. A raster according to claim 1, wherein the channels for X-ray transporting are filled with light metal.

8. A raster according to claim 1, wherein the channels for X-ray transporting are filled with an organic material.

9. A raster according to claim 1, wherein the channels for X-ray transporting are formed of glass mono or polycapillaries.

10. A raster according to claim 9, wherein the walls of the channels for X-ray transporting comprise lead glass.

11. A raster according to claim 1, wherein said raster comprises a parallelepiped cells, formed by the channels.

12. An anti-scatter X-ray raster, for placing between a radiation detector and an object under study, said raster comprising:

a plurality of tubular channels for X-ray transporting, walls of said tubular channels comprising a material capable of absorbing X-rays, wherein an orientation of said walls of said tubular channels changes from the center of the raster to a periphery of the raster, wherein said walls of said tubular channels form truncated cones or truncated pyramids with a common top and form a honeycomb structure, said walls of the neighboring channels are fused with each other;

inputs and outputs of said channels are placed on two concentric spherical surfaces with a center coinciding with said common top of the truncated cones or truncated pyramids, the walls of neighboring channels are spliced with each other such that the largest cross size d of a single channel for and its length H meet a relationship $2d/H > \theta_c$, where $\theta_c = \hbar\omega_p/E$ is the critical angle of total external reflection of X-rays from the walls of the channels transporting X-rays, for the material of the walls, $\hbar$ is the Planck constant.

$\omega_p$ is the plasma frequency of the material of the channels' walls,

E is energy of radiation quanta.

13. A raster according to claim 12, wherein the walls of the channels for X-ray transporting comprise lead glass.

14. A raster according to claim 12, wherein the walls of the channels for X-ray transporting comprise metal.

15. A raster according to claim 12, wherein the walls of the channels for X-rays transporting comprise heavy metal.

16. A raster according to claim 12, wherein the walls of the channels for X-ray transporting comprise a dielectric.

17. A raster according to claim 12, wherein the channels for X-ray transporting are hollow.

18. A raster according to claim 12, wherein the channels for X-ray transporting are filled with light metal.

19. A raster according to claim 12, wherein the channels for X-ray transporting are filled with an organic material.

20. A raster according to claim 12, wherein the channels for X-ray transporting comprise glass mono or polycapillaries.

21. A raster according to claim 20, wherein the walls of the channels for an X-ray transporting are made of lead glass.

22. A raster according to claim 12, wherein said raster is formed as a narrow parallelepiped of cells, formed of the channels for X-ray transporting.

23. An anti-scatter X-ray raster, for placing between a radiation detector and an object under study, comprising:

a plurality of tubular channels for X-ray transporting, walls of the said channels comprising a material being capable of absorbing X-rays, wherein an orientation of the walls changes from a center of the raster to a periphery of the raster, wherein the walls of the tubular channels form truncated cones or truncated pyramids with a common top and form a honeycomb structure, said walls of the neighboring channels are fused with each other; and inputs and outputs of said tubular channels are placed in two parallel planes, which are perpendicular to an axis of one of the tubular channels, placed in the central zone of the raster, the walls of the neighboring channels are spliced with each other, wherein the largest cross size d of a singe channel for an X-rays transporting and its length H meet a relationship satisfy the correlation:

$$2d/H > \theta_c,$$

where $\theta_c = \hbar\omega_p/E$ is the critical angle of total external reflection of X-rays from the walls of the channels transporting X-rays, for the material of the walls, $\hbar$ is the Planck constant, $\omega_p$ is the plasma frequency of the material of the channels' walls, E is energy of radiation quanta.

24. A raster according to claim 23, wherein the walls of the channels comprise lead glass.

25. A raster according to claim 23, wherein the walls of the channels comprise metal.

26. A raster according to claim 23, wherein the walls of the channels comprise heavy metal.

27. A raster according to claim 23, wherein the walls of the channels comprise a dielectric.

28. A raster according to claim 23, wherein the channels are hollow.

29. A raster according to claims 23, wherein the channels are filled with light metal.

30. A raster according to claim 23, wherein the channels are filled with an organic material.

31. A raster according to claim 23, wherein the channels are formed of glas~mono or polycapillaries.

32. A raster according to claim 31, wherein the walls of the channels comprise lead glass.

33. A raster according to claim 23, wherein said raster is made parallelepiped of cells formed by the channels.

* * * * *